(12) United States Patent
Meisberger

(10) Patent No.: US 6,362,887 B1
(45) Date of Patent: Mar. 26, 2002

(54) DEVICE FOR MEASURING CHANGES IN PARAMETERS WITHIN TRANSPARENT OBJECTS

(75) Inventor: Artur Meisberger, St. Wendel (DE)

(73) Assignee: Fresenius AG, Bad Homburg (DE)

( * ) Notice: Subject to any disclaimer, the term of this patent is extended or adjusted under 35 U.S.C. 154(b) by 0 days.

(21) Appl. No.: 09/327,822

(22) Filed: Jun. 8, 1999

(30) Foreign Application Priority Data

Jun. 8, 1998 (DE) .......................................... 198 25 518

(51) Int. Cl.[7] .............................................. G01N 21/27
(52) U.S. Cl. ...................................... 356/411; 356/436
(58) Field of Search .................................. 350/130, 432, 350/435, 436, 343, 141, 442, 409, 410, 411, 128, 39

(56) References Cited

U.S. PATENT DOCUMENTS

| 3,591,801 A | * | 7/1971 | Watson ........................ 356/433 |
| 3,999,856 A | * | 12/1976 | Unterleitner ................ 356/130 |
| 5,602,647 A | * | 2/1997 | Xu et al. ..................... 356/435 |
| 5,644,402 A | | 7/1997 | Chevallet |

FOREIGN PATENT DOCUMENTS

| DE | 41 32 965 | 4/1993 |
| EP | 0 634 642 | 1/1995 |

* cited by examiner

Primary Examiner—Richard A. Rosenberger
(74) Attorney, Agent, or Firm—Kenyon & Kenyon

(57) ABSTRACT

A device is described for measuring changes in parameters in transparent objects, in particular for medical applications. For universal use in various applications, the device includes a light source, an optical line sensor which detects the intensity of the light of the light source passing through the object as a function of location in at least one extension direction of the object, and a computer unit which compares the distribution of the light intensities detected by the optical line sensor as a function of location with at least one predetermined reference distribution. According to another embodiment, the light source supplies approximately parallel light, and the computer unit shapes the first derivation according to location of the distribution of the light intensities detected by the optical line sensor. The device is designed so that the different light sources can be easily replaced or combined.

35 Claims, 4 Drawing Sheets

DEVICE FOR MEASURING CHANGES IN PARAMETERS WITHIN TRANSPARENT OBJECTS

FIELD OF THE INVENTION

The present invention relates to a device for measuring changes in parameters within transparent objects.

BACKGROUND INFORMATION

There is a demand, in particular in medical applications, for detection of different parameters of fluids stored in containers and/or passed through tubing.

U.S. Pat. No. 5,644,402 discloses an optical measurement device for detecting red blood cells, which can be used, in particular, in an artificial kidney. The measurement device has an infrared transmitter, an infrared receiver and two mirrors, which are arranged around a length of medical tubing in such a way that when the tubing is empty, the light emitted goes to the receiver by simple reflection. If the tubing is filled with blood, the light emitted reaches the receiver at least partially by multiple reflection due to refraction. Since multiple reflection occurs only in the presence of red blood cells, it is possible with this device to detect even the lowest concentrations of blood in a fluid.

European Patent Application No. 634,642 A1 discloses an optical measurement device for measuring concentrations of certain substances such as glucose, red blood cells, or proteins in fluids. The measurement principle is based on the Lambert-Beer law which describes the relationship between the concentration of a solution and its light absorption. Consequently, the measurement device has a light source which supplies approximately parallel light, a measurement object with a variable optical path length and an optical sensor which detects the intensity of the light from the light source passing through the object for various optical path lengths. Devices are provided which permit multiple measurements for different optical path lengths at one time as well as devices with which only one optical path length can be measured at one time. The signals of the optical sensor are analyzed by a computer unit in which the Lambert-Beer law is implemented.

German Patent Application No. 41 32 965 A1 discloses an optical measurement device which detects the separation boundary between red blood cells and blood plasma in a blood centrifuge, where a light source is directed at the components in a blood centrifuge and the reflected light is picked up by an optical line sensor. The signals received by the line sensor are relayed to a computer unit where a brightness between the blood plasma and the red blood cells is analyzed. A control unit is driven according to the brightness, causing a plasma pump to be operated until a certain brightness limit can no longer be detected and there are only red blood cells in the blood centrifuge.

One disadvantage of the above-described optical measurement devices is that a special design must be provided for each application, which necessitates special adjustments and new developments for product series with different sensors for each product, which ultimately leads to higher costs on the whole.

SUMMARY OF THE INVENTION

An object of this invention is to create an optical measurement device which can be used universally for various applications.

A first embodiment of the present invention includes a device for measuring changes in parameters within transparent objects, in particular for medical applications, with a light sensor, with an optical line sensor detecting the intensity of the light from the light source passing through the object as function of the location in at least one extension direction of the object, and with a computer unit which compares the distribution of the light intensities detected by the optical line sensor as a function of the location with at least one predetermined reference distribution.

This embodiment according to the present invention is based on the finding that with this arrangement, a wide variety of optical parameters of a transparent object can be analyzed by the computer unit. Possible parameters may include turbidity, coloration, scattering, optical refraction, irregularities in the object as well as the motion or size of particles. Stored in the computer unit is at least one predetermined reference distribution so that the light intensities detected by the optical line sensor can be compared as a function of location. The reference distribution is preferably recorded once before the actual measurement on the basis of an object with known parameters. Thus in this way, changes in parameters can be determined easily with respect to the known object without requiring an absolute determination of the respective parameters. This also has the advantage that the same disturbance variables are averaged out in the device in recording the reference distribution and in the actual measurement.

According to a preferred embodiment, the light source is a point light source. Such a light source has a beam of light emitted in the direction of the optical line sensor. With objects with parallel bordering faces which also extend parallel to the optical line sensor, use of a point light source has the advantage that a defined optical refraction can be established on the parallel walls. In addition, due to the inverse-square law, a characteristic intensity distribution which is especially suitable for comparison with a predetermined reference distribution is obtained on the optical line sensor.

According to another preferred embodiment, however, a light source which supplies approximately parallel light may also be used. Such a light source in turn makes use of the fact that there happens to be no optical refraction on an object with parallel walls aligned perpendicular to the parallel beams of light. Thus, optical refraction can be prevented in a controlled manner with such a light source if there happens to be no interest in this parameter.

The two types of light sources also may be used together in combination. In this case, the analysis of the light from the light sources can be performed with a time offset, in which case the other light source is then turned off. However, a simultaneous analysis of both light sources with two optical line sensors may occur if crosstalk of the light of the two light sources is avoided through appropriate partitions.

The optical line sensor preferably has a CCD sensor (CCD=charge coupled device). With such a sensor it is possible to determine the light intensities in one extension direction as well as in two extension directions of the respective objects. If a two-dimensional CCD sensor is used, the device according to the present invention functions accordingly if a two-dimensional reference distribution is used as the basis instead of a one-dimensional reference distribution. A two-dimensional determination of the light intensities may have the advantage that the respective changes in parameters can be determined even more accurately.

In each instance, the reference distributions are recorded on the basis of a reference object. The intensities are converted by an AD converter into digital values and stored in the computer unit. The computer unit usually has a microprocessor and/or a signal processor as well as memory units and peripherals connected to it. A reference distribution is preferably recorded first without any influence by an object or an "empty" object (e.g., an empty fluid line) between the light source and the optical line sensor and then stored in the computer unit. The object which is between the light source and the optical line sensor and has neutral optical properties is referred to below as the "dummy object."

With a reference distribution on the basis of a dummy object, changes in the measured light intensity on the optical line sensor can be detected. If the measurement of the light intensity is to be color-selective, the optical line sensor will usually have separate color sensors, in particular for the colors red, green and blue. Separate reference distributions are preferably recorded for each of these color sensors, so that there can be a color-selective change in light intensities as well. It is also possible to use color filters instead of color-sensitive sensors. This is also true of the use of polarization filters. If a certain coloration and/or polarization is of interest in an object, an especially accurate measurement can be performed by recording a reference distribution on the basis of an object with a known change in the color filter/polarization characteristics in comparison with the dummy object. The known color filter/polarization characteristic is obtained as soon as the greatest similarity between the distribution of the measurement object and this stored reference distribution is found on the basis of the comparison performed in the computer unit.

In addition, to measure a certain optical refraction of the object, preferably a reference distribution recorded on the basis of an object with a known change in optical refraction characteristic in comparison with the dummy object is stored in the computer unit. In an ongoing measurement, there are in particular two possibilities in this regard which can cause a change in the optical refraction properties on the object. First, a change in optical density of the object can cause a greater or lesser optical refraction of the light emitted by the light source. The point property of the light source is essential here, so that the light is emitted in a beam with respect to the object, thus yielding an optical refraction according to different incident angles of the light. Second, however, the geometric shape of the object may also change, thus also resulting in changes in optical refraction because of changes in the incident angle.

In addition, in order to measure a given light scattering on the object, preferably a reference distribution recorded on the basis of an object with a known change in the scattering characteristic in comparison with the dummy object is stored. In contrast to the optical refraction, the light scattering is based on the scattering on particles having an extension on the order of magnitude of the wavelength of the light. This yields a diffuse widening of the distribution recorded to include locations which would be in the shadow without the presence of scattering particles.

According to the parameters described above, it is also possible to proceed with other optical parameters to record other reference distributions.

Another possibility of providing the reference distributions is for at least one reference distribution to be based on a mathematical model. The mathematical model may be based, for example, on a curve shape analysis of values determined by the measurements. Inasmuch as the curve analysis is performed on the basis of the measurement curves described above, a considerable amount of memory can be saved in comparison with direct storage of the reference distributions determined by the measurements. Instead of individual measured values, however, it is necessary only to store a mathematical function which supplies the respective distribution location for a certain spot as needed. However, the mathematical model may also be based on theoretical relationships of the technical optics derived on the basis of the optical properties of the object.

The comparison in the computer unit between the recorded distribution of the object and the stored reference distribution in each instance preferably is performed on the basis of a correlation with the respective reference distribution. The correlation here is based on multiplication of the respective distributions for each location and a subsequent integration over all locations. The correlation value may be standardized expediently to the maximum correspondence, i.e., precisely when two corresponding reference distributions are assumed as the basis. This yields a percentage correlation value which allows a statement of the change in parameter on the object to be measured in comparison with the dummy object or the object on which the reference distribution is based. To obtain a relevant correlation value with measured distributions, where another parameter has been varied in addition to the weakening of intensity, it is suggested that the attenuation of intensity be determined merely on the basis of the integral of the recorded distribution in comparison with the integral of the reference distribution of the dummy object and that, with regard to the other distribution, the maximum recorded distribution be standardized to a common value with the respective reference distribution. In this way, the effect of the attenuation of intensity can be approximately eliminated in the correlation with another reference distribution.

In summary, the computer unit thus yields information corresponding to the result of the comparison regarding the changes in parameter compared to all the stored reference distributions and the objects on which they are based.

The device according to the present invention may be used preferably in medical technology, where the object here is preferably medical tubing carrying a liquid medium such as blood. To record certain reference distributions, the tubing may be filled with fluids having the known optical properties, or the tubing may be filled with fluids which are preferably to be detected. With a medium carried in medical tubing, another factor to be taken into account is that the properties of the medium flowing through the tubing may change constantly over time. Therefore, the measured changes in parameters are preferably stored as a function of time, with a dynamic change in the parameters of the liquid medium also being determined on the basis of the stored values.

In addition to a length of medical tubing, it is also possible for the measurement area to be designed as a film chamber, with a flexible film stretched over a few bordering faces or as a rigid cassette part. The object also may be a symmetrical, partitioned twin-chamber container filled with different media, with the partition being arranged in the plane of symmetry of the line sensor and the light source. Because of the symmetry of the device according to the present invention, it is thus possible to perform at the same time a measurement of changes in parameter compared to the dummy object separately for both chambers. With a two-dimensional CCD sensor, a container may be provided with multiple chambers accordingly. The measured parameter changes of the two chambers however also may be compared, in which case a liquid with known properties will be in one chamber. This makes it unnecessary to record a reference distribution for this liquid separately, but instead this reference distribution can be measured simultaneously with the measurement of the liquid in the other chamber.

A second embodiment of the present invention includes a device for measuring changes in parameters on transparent objects, in particular for medical applications, with a light source that supplies approximately parallel light, with an optical line sensor which detects the intensity of the light of the light source passing through the object as a function of the location in at least one extension direction, and with a computer unit for farther processing of the light intensities detected by the optical line sensor.

In contrast with the first embodiment, the light source in the second embodiment is limited to a light source with approximately parallel light. If the object has straight-line bordering faces which are introduced between the light source and the optical line sensor perpendicular to the beam path of the light source, optical refraction effects are eliminated. If the object also does not have any scattering properties, direct shadow imaging on the optical line sensor is thus achieved by the parallel light. Thus one need not rely on a comparison with a predetermined reference distribution in the computer unit.

According to a preferred embodiment, the first derivation according to the location is shaped in the computer unit from the distribution of light intensities detected by the optical line sensor. This arrangement is thus very suitable for analysis of material inclusions or other inhomogeneities in the object without having to take into account any falsifying effects due to scattering or refraction. Since the first derivation according to location yields especially high values due to material inclusions or other inhomogeneities at the shadow boundaries, a simple analysis can be performed in this way without having to perform a reference measurement first.

According to a preferred embodiment, the object is a multichamber container whose chamber partitions run parallel to the path of light of the light source, with the chambers being filled with different media. In this way, the light absorption of different media can easily be analyzed and compared. In particular, an analysis according to different color values can also be performed if the optical line sensor has separate color sensors, e.g., for the colors red, green and blue, as mentioned above.

According to the present invention, the local assignment of the partitions is determined on the basis of the first derivation according to location. This is possible because the partitions cause high values in the first derivation according to location due to their low light-transmitting capacity in comparison with the chambers. In this way, it is thus superfluous to perform an accurate spot fixation in relation to the optical line sensor and the multichamber container. After the local assignment of intensity signals to each chamber has been determined, the light intensities detected for a given chamber are expediently averaged for comparison with the averaged light intensities of other chambers.

Another possibility is for the object to be length of medical tubing through which a liquid medium such as blood is passed. An air bubble detector, for example, for medical applications can be constructed with this arrangement.

A special advantage of the device according to the first and second embodiments of the present invention is that the same electronic components comprising the optical line sensor and the computer unit can be used for both embodiments. In addition, a relatively simple and inexpensive light source for which no imaging optics are needed can be used. It is especially advantageous to provide a holder for both embodiments to which a point light source and/or a light source that supplies approximately parallel light can be attached. This makes it possible to implement the embodiments according to the present invention with only one device.

First, the holder may be designed so that a point light source can be replaced with a light source supplying approximately parallel light, depending on the application. The same also applies to the converse case, so that the measurement device need not be modified from the basic design. Second, however, it is also possible to mount both a point light source and a light source supplying approximately parallel light on the holder. In this way, the possibilities of the two embodiments described above can be combined. This can be accomplished first by turning on the light sources with a time offset and by analyzing the light intensities separately by an optical line sensor. However, it is also possible to use two line sensors to be able to perform a separate analysis of the two light sources at the same time, but in that case, optical crosstalk between the two light beams of the two light sources must be prevented by an appropriate optical separation.

With regard to the embodiment of the holder, it must also be pointed out that the light source and the sensor can be arranged not only directly opposite one another but also at a certain angle to one another. For example, it is possible to measure signals only on the basis of the scattering and turbidity of a medium with a right angle arrangement and avoiding direct illumination of the sensor.

Thus, on the whole with the first and/or second embodiments according to the present invention, an optical measurement device is created which can be used universally for a great variety of applications without having to specially adapt the respective measurement device in a costly manner for each application. The measurement device according to the present invention can thus be produced in much larger numbers and therefore inexpensively.

A transparent object as defined herein means an object which permits at least some light to pass through it.

BRIEF DESCRIPTION OF THE DRAWINGS

Additional properties and advantages of the present invention will now be explained in greater detail on the basis of the embodiments illustrated in the drawings, in which.

DETAILED DESCRIPTION

Figure 1:
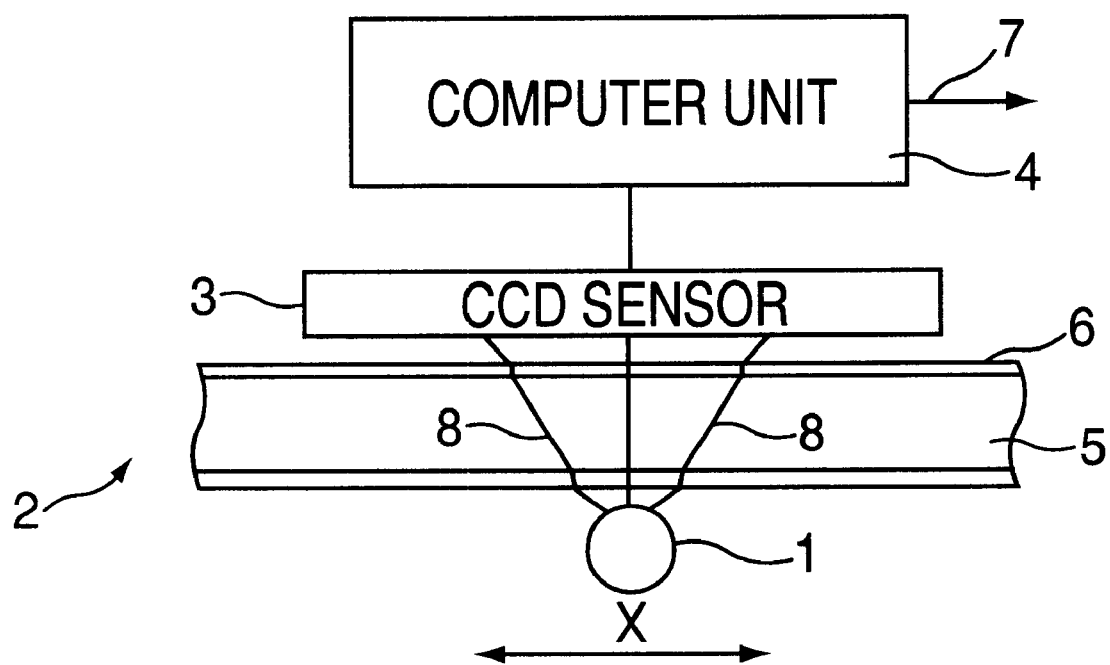
FIG. 1 shows a measurement device of the present invention according to the first embodiment with a length of medical tubing as the object.

FIG. 1 shows a measurement device according to the first embodiment with a length of medical tubing as the object. In its basic design, the measurement device comprises a CCD sensor 3 whose signals are analyzed by a computer unit 4. The result of this analysis is output over output channel 7 for further analysis or display. CCD sensor 3 and computer unit 4 are accommodated in a housing and form a unit which can be used equally for all applications. A holder on which is mounted a point light source 1 is also in a fixed location arrangement with respect to the housing. Between light source 1 and CCD sensor 3 there is a measurement object 2, which in this case is a length of medical tubing 6 conveying a liquid medium 5. Beams of light 8 emanate from light source 1, pass through object 2 and then strike CCD sensor 3.

Depending on the thickness and the optical density of tubing sheathing 6 and the optical density of medium 5, the beams of light 8 are refracted in a characteristic manner in passing through object 2. Furthermore, there may be additional effects due to turbidity, coloration, scattering particles, irregularities or shadow-forming particles in the medium. These irregularities are the parameters that are to be determined in the medium. The analysis is explained here on the basis of FIG. 2.

The analysis is based essentially on the fact that before the actual measurements, different reference distributions are recorded on the basis of objects with known optical properties with which the distribution of the light intensities detected by the optical line sensor during the measurement is compared as a function of the location. The comparison is preferably performed on the basis of a correlation which is based on multiplication of the individual values with subsequent integration. In addition to determination of the reference distributions with measurements, it is also possible to base this on mathematical models on the basis of which the reference distributions can be determined. The mathematical models may in turn be based on a curve shape analysis of values obtained by measurements or based on the physical laws of optics.

Figure 2A:
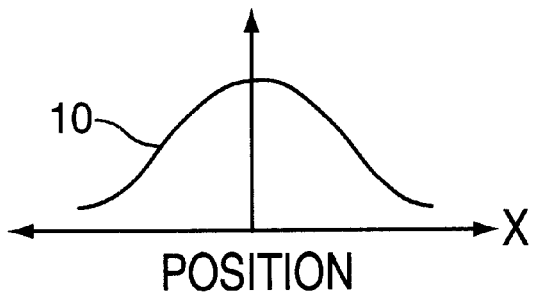
FIG. 2a shows a reference distribution which was recorded without influence by an object between the light source and the optical line sensor.

FIG. 2a shows a reference distribution recorded without the effect of an object between a light source and an optical line sensor. The object with neutral optical properties between the light source and the CCD sensor is known as a dummy object. Reference distribution 10 in FIG. 2a shows a Gaussian distribution on the basis of the point light source according to the inverse-square law.

Figure 2B:
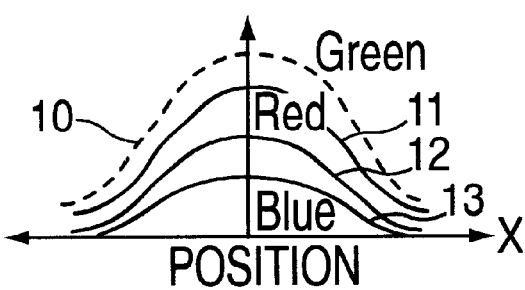
FIG. 2b shows separate distributions for the colors red, green and blue with a colored object.

FIG. 2b shows the relationships in a pure color measurement of an object. The object affects the beam path only with regard to the color intensities, as could be the case with a thin filter disk, for example. CCD sensor 3 has separate color sensors for each of the colors red, green and blue for which distributions 11, 12 and 13 were recorded. These are attenuated in comparison with reference distribution 10 according to FIG. 2a. The color of the object can be deduced from the respective attenuation in comparison with reference distribution 10.

Figure 2C:
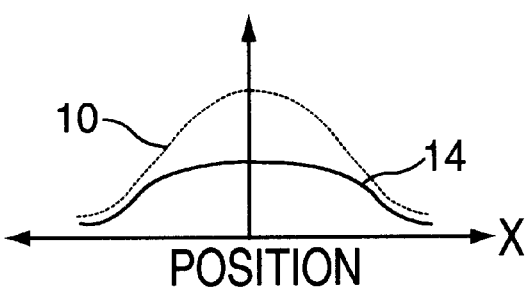
FIG. 2c shows a reference distribution on the basis of an object with a known scattering characteristic.

FIG. 2c shows a reference distribution on the basis of an object with a known scattering characteristic. Scattering occurs on particles having an extension on the order of magnitude of light. With particles in a uniform random distribution in a medium passing through a length of tubing according to FIG. 1, a reproducible widening or flattening of the measured intensity distribution occurs. Such a distribution 14 is plotted in comparison with the reference distribution 10 of a dummy object.

Figure 2D:
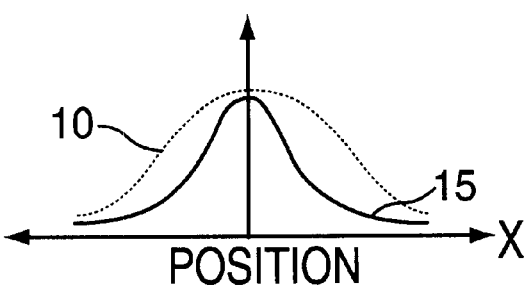
FIG. 2d shows a reference distribution on the basis of an object with a known optical refraction characteristic.

FIG. 2d shows in a corresponding diagram a reference distribution 15 based on an object with a known optical refraction characteristic in comparison with a reference distribution 10 based on a dummy object. As indicated in FIG. 2d, an optical refraction resulting in a corresponding concentration of the intensity distribution occurs toward the center of the CCD sensor in optical refraction according to the optical density of the medium.

Figure 2E:
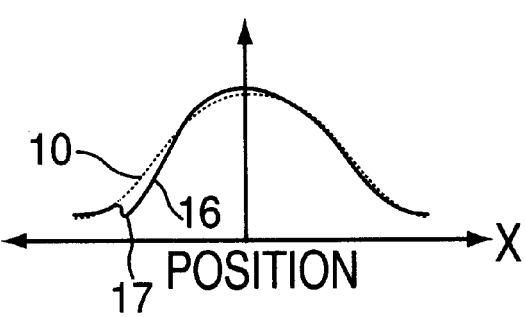
FIG. 2e shows a measured distribution on the basis of an object with incorporated particles or irregularities.

FIG. 2e shows a measured distribution on the basis of an object with incorporated particles or irregularities. Measured distribution 16 has a very high correlation with the corresponding reference distribution 10, so that an additional curve shape analysis is necessary to be able to detect the irregularity at position 17. This curve shape analysis may be based, for example, on the first derivation according to the location of distribution 16, with high values of the first derivation being obtained in the area of position 17.

If reference distributions 10, 14 and 15, which are shown here as examples, are stored in the computer unit, a comparison with a distribution actually measured is performed preferably on the basis of correlation analysis. The correlation value of two distributions is calculated by multiplication of the individual values and subsequent integration. The correlation value is expediently standardized to the eigen-correlation of the respective distribution, so that a value of 100% is established as the maximum relative correlation value. To determine the individual correlation values, first the integral light intensity of the measured distribution is determined. This integral is compared with the integral of reference distribution 10, to thus obtain information regarding the light absorption of the object. In a color analysis, this is done separately for all colors according to FIG. 2b. Before a correlation with the other reference distributions 14 and 15, the measured distribution is standardized to the maximum of the reference distribution to be correlated, in order to thereby eliminate the effect of light absorption. In another step, the correlation with reference distributions 14 and 15 is performed. Then, the scattering or optical refraction of the respective object is deduced on the basis of the relative correlation values.

Figure 3:
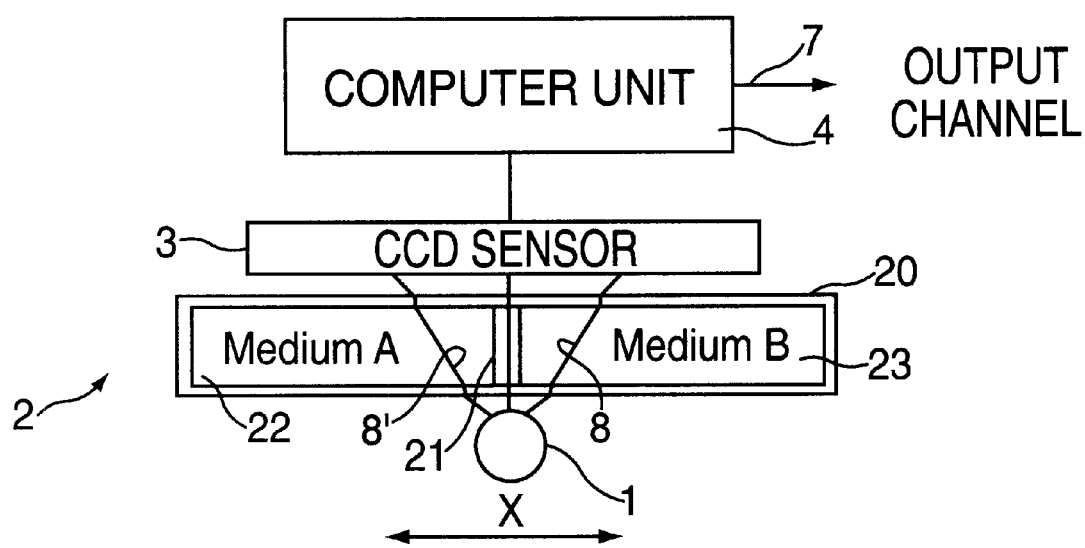
FIG. 3 shows a measurement device according to the first embodiment with a twin-chamber container as the object.

FIG. 3 shows a measurement device according to the first embodiment with a twin-chamber container as the object. In comparison with the device in FIG. 1, the device in FIG. 3 differs in that object 2 is a twin-chamber container 20. The twin-chamber container has a partition 21 which is in the line of symmetry between light source 1 and CCD sensor 3. Twin-chamber container 20 is also symmetrical with partition 21, to guarantee the same optical properties between the two chambers with regard to geometry. The two chambers are filled with different media 22 and 23. First, analysis may be performed as described according to FIGS. 1 and 2, where media 22 and 23 can be analyzed at the same time. Secondly, however, a direct comparison between the two media can also be performed.

Figure 4:
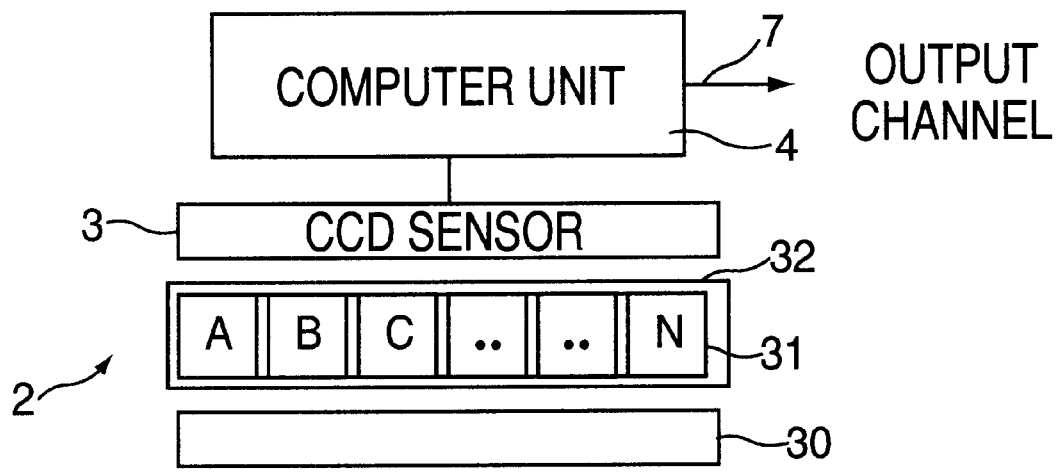
FIG. 4 shows a measurement device according to the second embodiment with a multichamber container as the object.

FIG. 4 shows a measurement device according to the second embodiment with a multichamber container as the object. Point light source 1 according to FIGS. 1 and 3 is replaced by a light source 30 which supplies approximately parallel light. The exchange of the two light sources is performed using the aforementioned holder which is not described in greater detail. Multichamber container 32 is divided into multiple chambers 31, which are filled with different media. With this device it is easily possible to compare the light absorption of different media without having to take into account the effects due to refraction.

Figure 5:
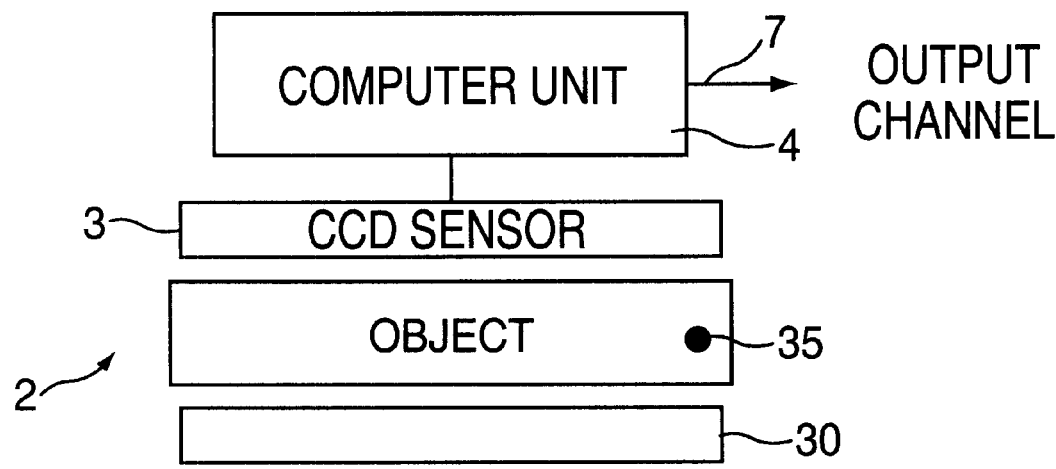
FIG. 5 shows a measurement device according to the second embodiment with a length of medical tubing as the object for detecting air bubbles.

FIG. 5 shows a measurement device according to the second embodiment with a length of medical tubing as the object for detection of air bubbles. In comparison with FIG. 4, the device according to FIG. 5 differs in that object 2 is a length of medical tubing extending in parallel between CCD sensor 3 and light source 30. A liquid in which air bubbles 35 can easily be detected is passed through the length of tubing.

The analysis in the computer unit according to the devices in FIGS. 4 and 5 does not rely on certain reference distributions as in the first embodiment. With a corresponding geometry of the object, optical refraction can be ruled out, so that the analysis is preferably performed on the basis of the first derivation according to the location of the light intensities detected. At high values of the first derivation, irregularities in the object can be deduced. In this way, the partitions of the multichamber container can be detected with the device according to FIG. 4, and air bubbles 35 can be detected with the device according to FIG. 5.

What is claimed is:

1. A device for measuring changes in parameters within transparent objects comprising:
   a light source for passing light through an object, the object having at least one extension direction;
   an optical line sensor for detecting a distribution of light intensities from the light passing through the object as a function of a location in the at least one extension direction; and
   a computer unit for comparing the distribution of the light intensities to at least one predetermined reference distribution.

2. The device according to claim 1 wherein the optical line sensor is a CCD sensor.

3. The device according to claim 1 wherein the light source is a point light source.

4. The device according to claim 1 wherein the light source is an approximately parallel light source.

5. The device according to claim 1 wherein the computer unit has a processor for storing at least one predetermined reference distribution.

6. The device according to claim 1 wherein the at least one reference distribution is a function of another object with a known change in an optical refraction characteristic.

7. The device according to claim 1 wherein the at least one reference distribution is a function of another object with a known change in a scattering characteristic.

8. The device according to claim 1 wherein the optical line sensor includes separate color sensors to measure a coloration of the object.

9. The device according to claim 8 wherein the separate color sensor include color sensors for red, green and blue.

10. The device according to claim 8 wherein the at least one reference distribution is a function of another object with a known change in a color filter characteristic.

11. The device according to claim 1 wherein the at least one reference distribution is a function of a mathematical model.

12. The device according to claim 11 wherein the mathematical model is a function of a curve shape analysis.

13. The device according to claim 12 wherein the curve shape analysis is a function of measurement curves.

14. The device according to claim 1 wherein the computer unit has a processor for comparing as a function of a correlation, a parameter change on the object being determined as a function of a strength of the correlation.

15. The device according to claim 1 wherein the object is a length of medical tubing.

16. The device as recited in claim 15 wherein the medical tubing is medical tubing suitable for transporting blood.

17. The device according to claim 15 wherein the computer unit include a processor for storing measured changes in parameters as a function of time and for detecting a dynamic change in the parameters of the liquid medium.

18. The device according to claim 1 wherein the object is a container having a first chamber, a second chamber and a partition, the object being symmetrical about the partition, the partition lying in a plane of symmetry of the line sensor and the light source.

19. The device according to claim 18 wherein the computer unit includes a processor for measuring at the same time changes in a parameter in the first chamber and the second chamber.

20. The device according to claim 18 wherein the computer unit includes a processor for measuring the first chamber so as to form the distribution of light intensities and for measuring another distribution of light intensities in the second chamber so as to form the at least one predetermined reference distribution.

21. The device according to claim 1 further comprising a holder for the light source.

22. A device for measuring changes in parameters within transparent objects comprising:
   a light source for supplying approximately parallel light;
   an optical line sensor for detecting and intensity of light of the light source passing through an object as a function of a location in at least one extension direction of the object; and
   a computer unit for further processing of the intensity of the light detected by the optical line sensor, wherein the computer unit includes a processor for forming a first derivative according to the location.

23. The device according to claim 22 wherein the object is a container having a first chamber, a second chamber and a partition, the partition being parallel to a path of the light of the light source.

24. The device according to claim 23 wherein the computer unit includes a processor for averaging light intensities detected between the partition and a second of the first chamber and comparing the averaged light intensities to averaged light intensities of the second chamber.

25. The device according to claim 22 wherein the object is a length of medical tubing.

26. The device according to claim 25 wherein the medical tubing is suitable for transporting blood.

27. The device according to claim 25 wherein the computer unit includes a processor for analyzing material inclusions or other inhomogeneities as a function of values of a first derivative of the location.

28. The device according to claim 22 further comprising a holder for the light source.

29. A method for measuring changes in a parameter within transparent objects comprising the steps of:
   passing light through an object having at least one extension direction;
   detecting a distribution of light intensities from the light passing through the object as a function of a location in the at least one extension direction; and
   comparing the distribution of the light intensities to at least one predetermined reference distribution.

30. The method according to claim 29 further comprising storing the at least one predetermined reference distribution in the computer unit.

31. The method according to claim 29 further comprising storing the at least one reference distribution in the computer unit, the at least one reference distribution not being affected by a dummy object.

32. The method according to claim 29 further comprising recording the at least one reference distribution as a function of another object with a known change in an optical refraction characteristic as compared to a dummy object.

33. The method according to claim 29 further comprising recording the at least one reference distribution as a function of another object with a known change in an optical refraction characteristic as compared to a dummy object.

34. The method according to claim 29 wherein the comparing step includes determining a change in a parameter determined on the object.

35. A method for measuring changes in parameters within transparent objects comprising the steps of:

supplying approximately parallel light;

detecting an intensity of light passing through an object as a function of a location in at least one extension direction of the object; and further processing the intensity of the light detected by the optical line sensor by forming a first derivative according to the location.

* * * * *